(12) United States Patent
Winkel Pettersson et al.

(10) Patent No.: US 7,413,658 B2
(45) Date of Patent: Aug. 19, 2008

(54) SEPARATION METHOD

(75) Inventors: Sylvia Winkel Pettersson, Vastra Frolunda (SE); Borje Persson, Agnesberg (SE); Mats Nystrom, Ytterby (SE)

(73) Assignee: Akzo Nobel N.V., Arnhem (NL)

( * ) Notice: Subject to any disclaimer, the term of this patent is extended or adjusted under 35 U.S.C. 154(b) by 276 days.

(21) Appl. No.: 10/904,670

(22) Filed: Nov. 22, 2004

(65) Prior Publication Data

US 2005/0133452 A1 Jun. 23, 2005

Related U.S. Application Data

(60) Provisional application No. 60/523,695, filed on Nov. 21, 2003.

(51) Int. Cl.
*B01D 15/08* (2006.01)
(52) U.S. Cl. ............... 210/635; 210/656; 210/198.2
(58) Field of Classification Search ............ 210/635, 210/656, 659, 198.2
See application file for complete search history.

(56) References Cited

U.S. PATENT DOCUMENTS

| | | | |
|---|---|---|---|
| 5,180,670 A | | 1/1993 | Iwata et al. |
| 5,277,813 A * | | 1/1994 | Feibush et al. ............ 210/502.1 |
| 6,241,891 B1 | | 6/2001 | Nagae |
| 6,841,073 B2 * | | 1/2005 | Nagae ..................... 210/635 |
| 6,926,823 B2 * | | 8/2005 | Kallury et al. ............ 210/198.2 |
| 6,966,992 B2 * | | 11/2005 | Hauser et al. ............ 210/656 |
| 7,125,492 B2 * | | 10/2006 | Bidlingmeyer et al. .... 210/635 |
| 2004/0112815 A1 | | 6/2004 | Nagae |
| 2005/0011836 A1 * | | 1/2005 | Bidlingmeyer et al. .... 210/656 |

FOREIGN PATENT DOCUMENTS

EP 0269080 A1 1/1988

OTHER PUBLICATIONS

Snyder (Introduction to Modern Liquid Chromatography, John Wiley, New York 1979, pp. 6-8 and 238-240).*
Przybyciel, et al., "Phase Collapse in Reversed-Phase LC," LC GC Europe, Oct. 2002, 652-657.
Enami, et al., "The Retention Behaviour . . . ", LC GC Europe, Jul. 2003, 418-425.
Herbert et al., "The HPLC Analysis of Polar . . . ", Poster presented at HPLC 2001, Maastricht, Netherlands, Jul. 2001.
Nagae, et al., "Retention Behaviour . . . ", Bunseki Kagaku, 0525-1931, Vol. 49, No. 11, Nov. 2000, 887-893 (abstract).
Zengbiao, et al., "Wetting of Octadecylsilylated Silica . . . ", Analytical Chemistry, vol. 68, No. 1, Jan. 1, 1996, 124-129.
Nagae, et al., "The Retention Behaviour . . . ", Presentation at the HPLC 2002 Conference.

(Continued)

*Primary Examiner*—Ernest G. Therkorn
(74) *Attorney, Agent, or Firm*—David J. Serbin; Robert C. Morriss

(57) ABSTRACT

The present invention relates to a method for separating products from a mixture by reversed phase high performance liquid chromatography using a column packed with a stationary phase which is hydrophobic and a mobile phase, wherein the loading step, during which the products to be separated are introduced in the column, is carried out with an aqueous phase while applying an overpressure of at least about 0.3 MPa.

17 Claims, 6 Drawing Sheets

OTHER PUBLICATIONS

Moller, et al., "Wettability Behaviour . . . ", Presentation at "Analysdagarna", May 2003.

Wolcott, et al., "Lessons in Column Washing", LC-GC, vol. 17, No. 4, Apr. 1999, 316-321.

Majors, et al., "Columns for Reversed-Phase LC . . . ", LC-GC Europe, Dec. 2002, 780-786.

Doschi, "A New Highly Stable Polar . . . ", CAST, Sep./Oct. 1999, 5-6.

* cited by examiner

SEPARATION METHOD

REFERENCE TO RELATED APPLICATIONS

This application claims the benefit of U.S. Provisional Application No. 60/523,695, filed Nov. 21, 2003.

The present invention relates to a method for separating products (compounds) from a mixture by reversed phase high performance liquid chromatography using hydrophobic stationary phases.

Reversed phase liquid chromatography is the most popular mode of high performance liquid chromatography (HPLC). However, the use of reversed phase HPLC materials with up to "100%" aqueous mobile phases can often cause problems of long equilibration times, reduced and irreproducible retention time, poor peak shape, reduced adsorption capacity and reduced quantitative reproducibility. Examples of poor peak shape are broad peaks and multiple peaks for the same substance. This can occur even when the elution phase contains a low content of organic modifiers of less than about 5%. This is the case, in particular, for separating water-soluble compounds. This phenomenon has widely been studied. Aqueous mobile phases are expelled from the pore system of hydrophobic stationary phases, resulting in a de-wetting of the stationary phase and leading to chromatography becoming more problematic, with retention loss, retention irreproducibility, increased tailing, and long gradient regeneration times. Typical hydrophobic stationary phases are, for example, alkyl-modified stationary phases such as C8-C30 alkyl-modifed ones.

M. Przybyciel R. E. Majors LC-GC Eur. 15(10) 652 (2002) describes phase collapse in reversed-phase LC and the wetting phenomenon. Furthermore, some problems associated with HPLC columns under 100% aqueous mobile-phase conditions are discussed by Toshiyaki Enami and Norikazu Nagae, Sid Doshi, LC-GC Eur. July 2003, pp 418-425. Parameters that affect the degree of de-wetting are described for example in S. Doshi, CAST Magazine, Issue 9, (1999), 5, and many manufacturing of HPLC packing material have addressed the problem by introducing different types of chemical substitution of silica, for example non-endcapped or polar endcapped bonded phases, or specially designed packing material with polar embedded alkyl chains (R. E. Majors, M. Przybyciel, LC-GC Eur., 15 (12), 780, (2002)).

These types of stationary phases suggested in the prior art above are often less hydrophobic, less durable and often leak stationary phase into the mobile phase. This leakage affects in particular preparative separations negatively.

Furthermore, it is generally difficult to load full amount of product mixture if they are present in a too low concentration. If products are present in an aqueous phase and solvents are added to improve the wetting of the stationary phase, it will loose some more of its ability to adsorb large amounts of products to be separated.

Another disadvantage is that if products are present in an aqueous phase and solvents are added to improve the wetting of the stationary phase, the products will be even more diluted.

Thus, there still exists a need for a method allowing the separation of products (compounds) on conventional hydrophobic stationary phases without the use of substantial amounts of organic modifiers which could be used for analytical separation but also for preparative separation with good separation with good reproducibility and good separation performance. Also, there still exists a need for a method allowing the separation of especially water-soluble products on conventional hydrophobic stationary phases which could be used for analytical separation but also for preparative separation with good reproducibility and good separation performance. Also, there is still a need for a method allowing the separation of products present in very low concentrations on conventional hydrophobic stationary phases which could be used for analytical separation but also for preparative separation with good reproducibility and good separation performance.

Surprisingly, the present invention makes it possible to use hydrophobic stationary phases for the separation of products (compounds) with high reproducibility and good retention thanks to a method in which the products (compounds) to be separated are loaded into the column in an essentially aqueous phase while applying a certain pressure on all parts of the stationary phase.

Also, surprisingly, the present invention makes it possible to separate products which are highly hydrophilic from a mixture without the need of adding ion-pair agents in order to make the compound to be separated more hydrophobic.

Also, surprisingly, the present invention makes it possible to separate very dilute products from a mixture. The present invention seems to give a very high affinity of products to the stationary phase, which makes it possible to accept more dilute sample solutions than otherwise would have been possible.

By "very dilute products" is herein meant products present in a concentration of less than about 0.1 weight %, suitably less than about 0.05 weight %, preferably less than about 0.02 weight %.

BRIEF DESCRIPTION OF THE DRAWINGS

The features and advantages of the present invention are well understood by reading the following detailed description in conjunction with the drawings in which like numerals indicate similar elements and in which.

DETAILED DESCRIPTION

The present invention provides a method for separating products (compounds) from a mixture by reversed phase high performance liquid chromatography comprising a loading step and a separation step, using a column packed with a stationary phase which is hydrophobic and a mobile phase (B), characterized in that the loading step is carried out with an aqueous phase (A) while applying an overpressure of at least about 0.3 MPa to all parts of the stationary phase in the column. The overpressure is suitably at least 0.4 MPa, also suitably from about 0.3 to about 10 MPa, preferably from about 0.4 to about 5 MPa, most preferably from about 0.5 to about 3.5 MPa.

The loading step is the step during which the products to be separated are introduced in the column.

According to the present invention, a hydrophobic stationary phase is a phase which has a higher affinity for organic mobile phases than for aqueous mobile phases. Examples of hydrophobic stationary phases are, for example, alkyl-modified stationary phases, suitably C8-C30 alkyl-, preferably C8-C18 alkyl-modified stationary phases. The hydrophobic stationary phase is preferably highly hydrophobic. The stationary phase can be based on both inorganic and organic materials. Suitable organic materials are porous polymer materials. Preferably, the stationary phase is a porous material based on an inorganic oxide such as alumina, titania, zirconia, chromia, silica, boria, toria, beryllia, silica-alumina and combinations thereof. Preferably, the stationary phase is porous silica. The stationary phase has preferably been modified to render its surface hydrophobic. Stationary phases of silica have preferably been modified to partly consist of $R_nSiX_{4-n}$ (n=1, 2 or 3), with each R consisting of an aryl group, an alkyl group or, in the case when n=2 or 3, a hydroxyl group, at least one R consists of an alkyl or aryl group. In the case n=2 or 3, each R may consist of the same or different groups. Preferred group(s) R, which are alkyl and aryl groups, are methyl, butyl, octyl, octadecyl, phenylethyl and phenylpropyl. Most preferably, at least one of R is octyl, octadecyl, phenylethyl or phenylpropyl. Furthermore, X consists of —O—Si where Si is a Si-atom which is either a part of the porous silica or a part of the added layer resulting from surface modification.

The pore size of the stationary phase is suitably from about 50 to about 500 Å, preferably from about 50 to about 150 Å.

In the present invention, the term "overpressure" means the pressure over the ambient pressure, which is atmospheric pressure. Thus, an overpressure of 2.5 MPa means an absolute pressure of about 2.6 MPa. Said overpressure can be obtained for example by including a pressure-regulating valve in the exit line from the column and to maintain at least a minimum flow through the column without interruption, as illustrated in the flow chart of FIG. 1.

Figure 1:
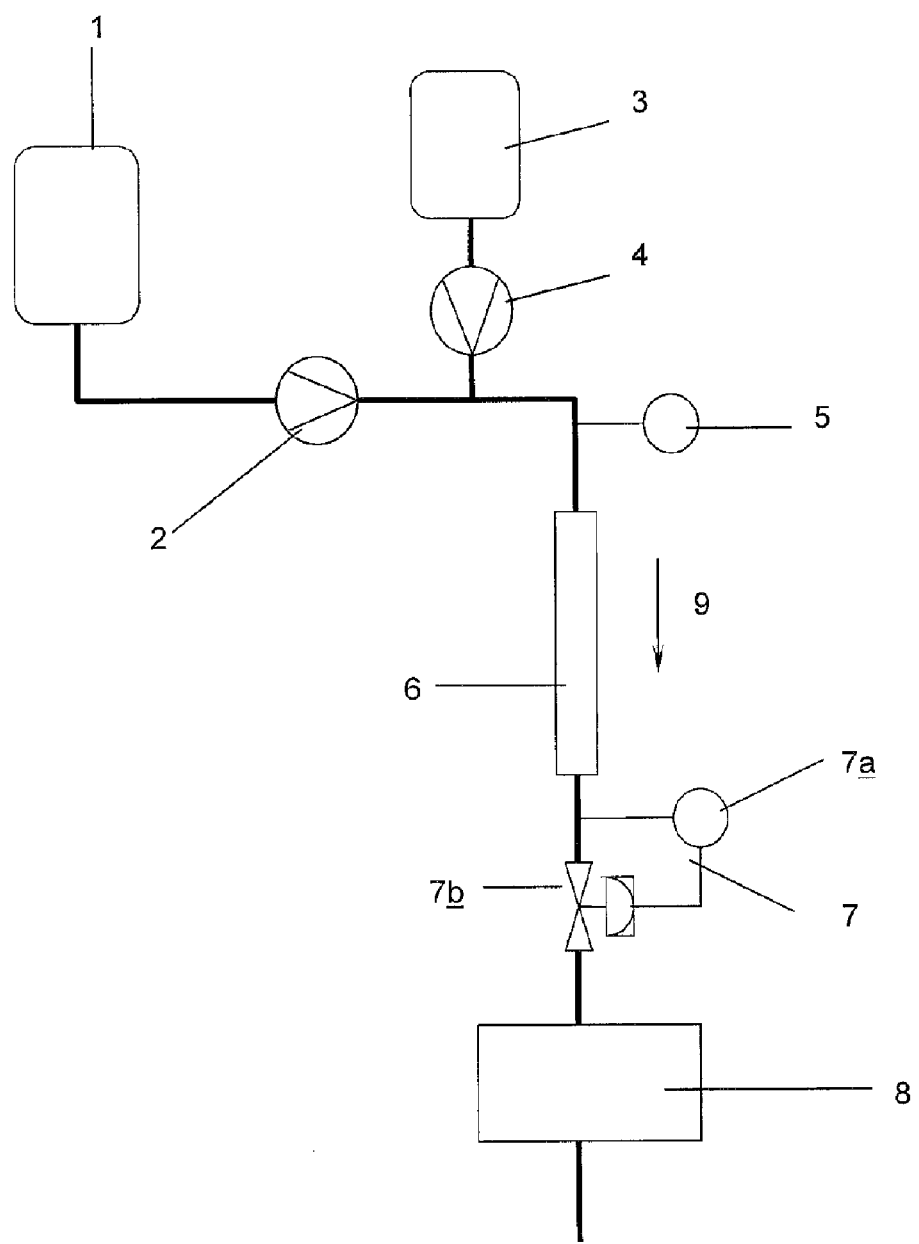
FIG. 1 is a schematic flow chart showing equipment for use in connection with a separation method according to an embodiment of the present invention.

In FIG. 1, it can be seen that the products to be separated are charged into a feed tank 3 and introduced into a column 6 by means of a pump 4, together with the mobile phase which is stocked in tank 1 and introduced in the column via pump 2. Products in solution in the mobile phase percolate through the column 6 in the direction 9 and separated products are detected through a monitor 8.

The system 7 allowing the maintenance of a constant minimum pressure in the column is illustrated by a regulating valve 7b placed downstream the column where the valve is arranged to control a measured pressure (gauge 7a) at the column exit. The pressure at the column entrance is measured via gauge 5.

The overpressure applied during the loading step will suitably depend on different factors such as the chemical nature of the stationary phase, in particular the length of the hydrocarbon chain, the nature of endcapping groups, if any, and the pore size. In particular, the overpressure will suitably be inversely proportional to the pore size.

According to the invention, the aqueous phase (A) is suitably a phase consisting essentially of water, preferably deionized water. Preferably, the aqueous phase (A) comprises an aqueous buffer. The aqueous phase (A) may also contain traces of an "organic modifier", which is suitably an agent increasing the mobile phase's affinity to products to be separated. The aqueous phase (A) may contain an organic modifier in concentrations suitably below 5% by volume, preferably below 1% by volume, preferably from about 0 to about 1% by volume, even more preferably from about 0 to about 0.5% by volume.

Suitable buffers are those conventionally used in the aqueous part of mobile phases used in chromatography in order to maintain the pH to a specified value. Suitable buffers can be aqueous solutions comprising combinations of one or more acidic and one or more basic components selected from the group consisting of trifluoroacetic acid (TFA) or other ion-pair forming acids, acetic acid, sodium hydroxide, potassium hydroxide, ammonia, tris(hydroxymethyl)aminomethane, phosphoric acid, sulfuric acid, and hydrochloric acid. The amount of buffer in the aqueous phase (A) is an amount conventionally used and is easy to determine by the person skilled in the art. The concentration of buffer is suitably up to about 1 mole/l, preferably from about 2 to about 300 mmole/l, most preferably from about 5 to about 200 mmole/l.

The aqueous phase (A) suitably comprises less than about 5% by volume of organic modifiers, preferably less than about 2% by volume, even more preferably less than about 0.5% by volume. Most preferably, the aqueous phase (A) is essentially free from organic modifiers.

The mobile phase (B) suitably essentially consists of water and an organic modifier.

According to a further embodiment of the method according to the invention, an organic modifier is added to the mobile phase (B) while maintaining the overpressure applied during the loading step.

The organic modifier is selected depending on the mixture of products to be separated, and is suitably chosen among those conventionally used in chromatographic separation methods.

The organic modifier is suitably selected from the group consisting of organic solvents miscible with water such as alcohols, ketones, esters and ethers. Preferably the organic modifier is selected from the group consisting of acetonitrile, methanol, ethanol, 1-propanol, 2-propanol, acetone, methylethylketone, ethyl acetate, tetrahydrofuran, dioxane and mixtures thereof.

The amount of organic modifier in the mobile phase (B) used in the separation step will also depend on the nature of the mixture to be separated but is suitably above 3% by volume, preferably above 5% by volume and even more preferably over 10% by volume. Suitably, the amount of organic modifier in the mobile phase (B) is from about 3 to about 95% by volume, preferably from about from about 5 to about 95% by volume, most preferably from about 10 to about 90% by volume.

The amount of organic modifier can be added progressively to the mobile phase (B).

According to a further preferred embodiment of the method according to the invention, the overpressure during the separation step is decreased while the amount of organic modifier increases. The overpressure can be decreased to zero, i.e., the column is then maintained under ambient pressure. The overpressure is suitably zero when the mobile phase (B) contains at least 3% by volume of organic modifier, preferably 5% and even more preferably 10%.

In any case, the overpressure is applied only when needed, i.e. during the loading step and the extra time used will be modest compare to the total duration of the different chromatographic separation steps.

In a further embodiment of the method according to the invention, which is very useful when the column has not been used for a long time, before the loading step, the column is flushed with an aqueous phase (C) comprising at least 15% by volume of an organic modifier, preferably at least 25% by volume, also preferably from about 15 to about 75% by volume, thereafter an overpressure of at least about 0.3 MPa, suitably from about 0.3 to about 10 MPa, also suitably at least 0.4 MPa, preferably from about 0.4 to about 5 MPa, most preferably from about 0.5 to about 3.5 MPa is applied to all parts of the stationary phase in the column and the mobile phase (C) is progressively substituted by an aqueous phase (A) while maintaining said overpressure.

According to a further preferred embodiment of the method according to the invention, it comprises the successive steps of:
- (a) flushing the column with a mobile phase (C) containing at least 15% by volume of an organic modifier;
- (b) applying an overpressure of at least about 0.3 MPa to all parts of the stationary phase in the column;
- (c) progressively changing the mobile phase (C) to an aqueous phase (A) while maintaining said overpressure;
- (d) loading the products to be separated in an aqueous phase (A) while maintaining said overpressure;
- (e) changing mobile phase from the aqueous phase (A) to a mobile phase (B) by adding an organic modifier while maintaining said overpressure;
- (f) elution with mobile phase (B) with reduced overpressure or after suppression of the overpressure;
- (g) completing the chromatographic separation.

The completion of the chromatographic separation is suitably carried out in a conventional way, suitably using gradients of elution.

As already indicated, the overpressure value depends on different parameters, such as the chemical nature of the stationary phase, in particular the length of the hydrocarbon chain, the nature of the endcapping groups if any, the particles diameter, the pore size.

In particular, the overpressure is suitably inversely proportional to the pore size.

For example, the overpressure applied to a C8-C18 surface modified stationary phase with a pore diameter of 100-120 Å may be of at least about 2.0 MPa, and with a pore diameter of 300 Å, it may be at least about 0.8 MPa. The C8-C18-surface modifications with high surface coverage and proper endcapping suitably require high overpressure of at least about 2.0 MPa for a pore size of 100-120 Å. Lower surface coverage and/or no endcapping may reduce the overpressure needed. C4- and other surface modifications will reduce or eliminate overpressure needed.

The time during which the overpressure is applied after the loading step is short in comparison with the duration of the chromatographic separation in itself.

The method according to the invention can, for example, be used for the separation of highly hydrophilic products. In particular, it is very useful for many preparative reversed phase separations for which it is an advantage if the crude feed solution can be loaded onto the column under highly aqueous conditions since this enables direct downstream processing from previous purification steps such as ion-exchange, without additional treatment such as desalting, dilution and concentration. For example, the method according to the invention allows the separation of mixtures of products selected from the group consisting of peptides, proteins, such as insulin, oxytocin, guanine and polynucleotides, prostaglandins, steroids, vitamins, pharmaceutical active compounds, such as amoxicillin, dopamin.

The present invention will be described in more detail in the following examples, which are given for illustrative purposes but are not limitative.

EXAMPLES

In the following examples, all chromatographic experiments were performed with a Waters 600E HPLC pump equipped with a Waters 486 UV detector (Waters, Milford, Mass., USA). The post-column pressure regulation valve was purchased from Alltech (Deerfield, Ill., USA). Buffers were prepared from deionized water from a MILLI-Q purification system (Millipore, Milford, Mass., USA) and were filtered through a 0.4 µm filter before use. Potassium dihydrogen phosphate and ammonium dihydrogen phosphate were purchased from Merck (Darmstadt, Germany), ammonium acetate and trifluoroacetic acid (TFA) from Fluka (Buchs, Switzerland). Acetonitrile was bought from Lab-Scan (Dublin, Ireland). All columns were 4.6 (I.D.)×250 mm and were obtained from Eka Chemicals AB, Bohus, Sweden. The columns used for this study were KR100-10-C8 and KR100-16-C18 (ligand density:, 3.7 (C8) and 3.5 (C18) µmol/m$^2$). Nominal pore size is 10 nm for these stationary phases. Average pore size (defined as 4×[pore volume/(BET surface area)]) were measured (before surface modification) and found to be 11 nm for both stationary phases.

Guanine, propylbenzene, human insulin and oxytocin were bought from Sigma-Aldrich (St. Louis, Mo., USA).

Example 1

Insulin Separations

This example shows that post-column pressure can be used to facilitate "100%" aqueous loading conditions for preparative peptide separations, a peptide, oxytocin (9 amino acids) and a protein, insulin (51 amino acids), were used.

A KR100-10-C8 column (4.6×250 mm, packing density: 0.6 g/mL) was equilibrated with 10 column volumes of the following aqueous phases:
- A: "100%" aqueous phase: water+0.1% TFA;
- B: water/acetonitrile 90/10 by volume+0.1% TFA;
- C: "100%" aqueous phase: 50 mM NH$_4$Ac at pH 4.5;
- D: (aqueous 50 mM NH$_4$Ac at pH 4.5)/acetonitrile 90/10 by volume, at 0.5 mL/min, with a post-column overpressure of 2.5 MPa only with mobile phases A and C.

Then 500 µL of human insulin solution (10 mg human insulin/mL water+0.1% TFA) was injected. Such an injection corresponds to a relative loading of 2 mg/g$_{packing\ material}$. The gradient elutions are shown in Table 1.

TABLE 1

| A) "100%" aqueous loading conditions (elutions A and C) | | | B) control (elutions B and D) | | |
|---|---|---|---|---|---|
| t [min] | flow [mL/min] | % by volume acetonitrile A/C | t [min] | flow [mL/min] | % by volume acetonitrile B/D |
| 0 | 0.5 | 0/0 | 0 | 0.5 | 10/10 |
| 15 | 0.5 | 0/0 | 15 | 0.5 | 10/10 |
| 15.1 | 0.5 | 10/10 | 15.1 | 0.5 | 25/26 |
| 30 | 0.5 | 10/10 | 95.1 | 0.5 | 33/34 |
| 30.1 | 0.5 | 25/26 | 140 | 0.5 | 33/34 |
| 110.1 | 0.5 | 33/34 | | | |
| 140 | 0.5 | 33/34 | | | |

Figure 2A:
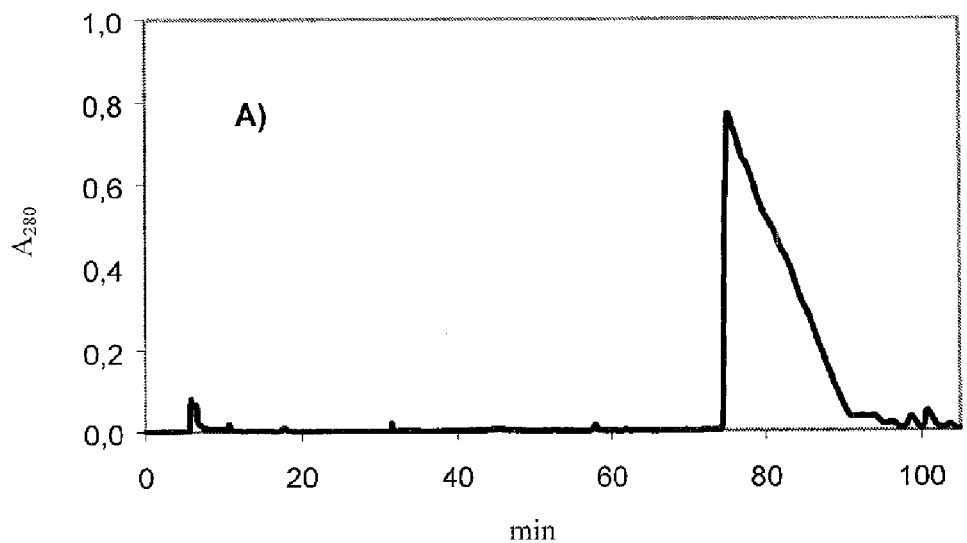
FIGS. 2A-5B are chromatograms obtained in connection with Examples described in the present application.

Chromatograms were recorded at 280 nm and are presented in FIG. 2, on which:

FIG. 2A. is the chromatogram obtained with mobile phase A as loading solution.

Figure 2B:
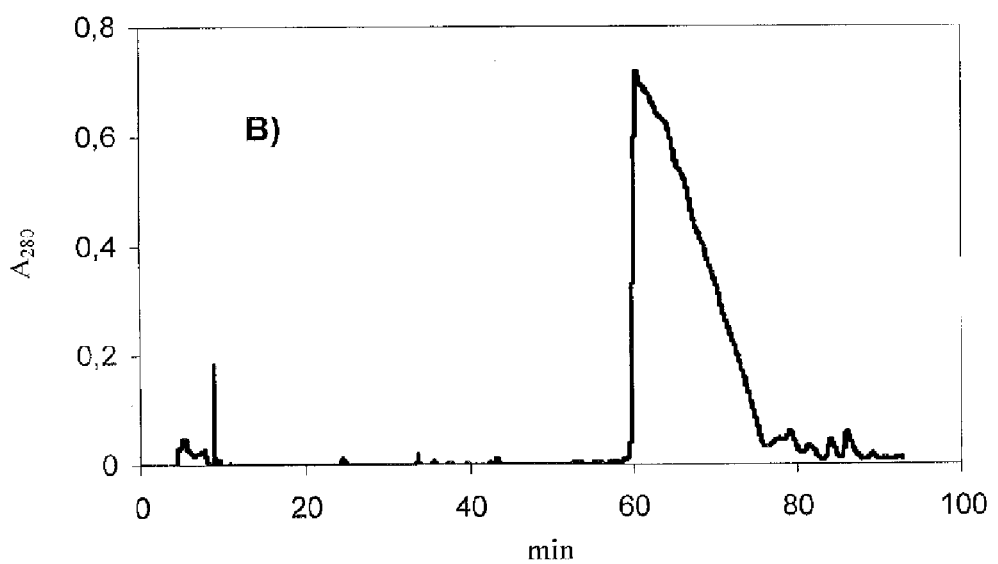

FIG. 2B. is the chromatogram obtained with mobile phase B as loading solution.

Figure 2C:
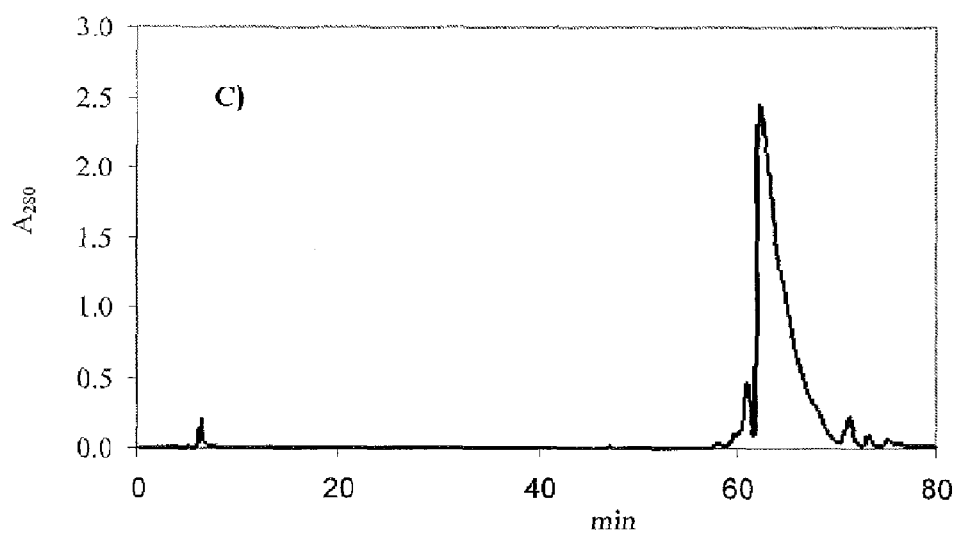

FIG. 2C. is the chromatogram obtained with mobile phase C as loading solution.

Figure 2D:
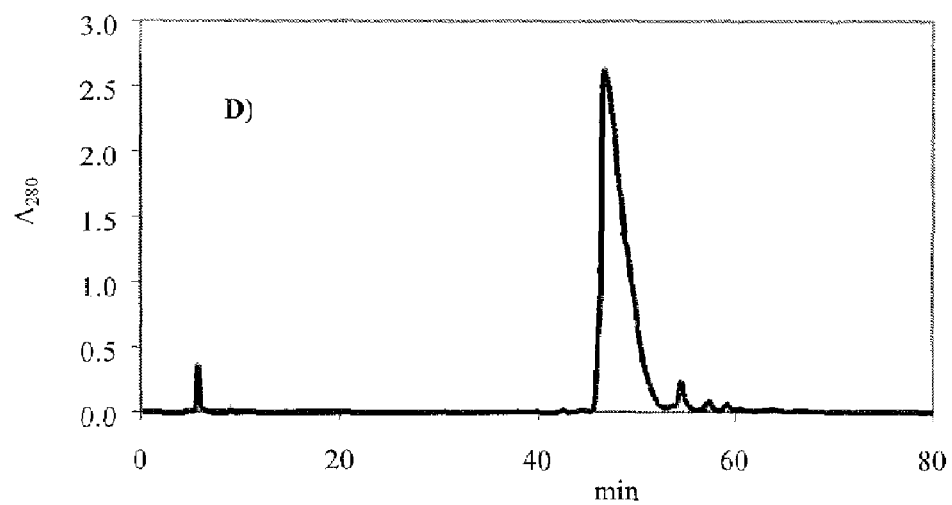

FIG. 2D. is the chromatogram obtained with mobile phase D as loading solution.

The retention times and peak widths of the peptides were compared between "100%" aqueous loading conditions (elutions A and C) and a control separation (elutions B and D) in which the column was equilibrated with 10% acetonitrile.

In the case of the "100%" aqueous conditions, a 2.5 MPa post-column overpressure was applied. As can be seen in, the moderately overloaded preparative injection of insulin was well retained on the C8 column when loaded under "100%" aqueous conditions. The difference in retention times between chromatogram A and B in FIG. 2 can be explained by an extra isocratic concentration step in separation A. Before the gradient was started, the column was purged 15 min with water+0.1% TFA, followed by another 15 min wash with water/acetonitrile 90/10 by volume+0.1% TFA. When recording the control chromatogram B, the column was only washed for 15 min with (water+0.1% TFA)/acetonitrile 90/10 by volume. The retention times were altered by only 4 min. In order to show that post-column pressure can be used in general to circumvent wettability problems during a loading step, ammonium acetate (elutions C and D) was tested as an alternative mobile phase buffer. Insulin was separated under the same conditions as those described above, and the peptide was again fully retained under "100%" aqueous loading conditions. Moreover, an impurity that co-eluted with the insulin peak when the loading was performed in 10% acetonitrile (elution D) could be separated entirely with a "100%" aqueous loading phase with 2.5 MPa overpressure (elution C)(see FIG. 2, chromatograms C and D).

Example 2

Oxytocin Separation

The same procedure as in example 1 was followed but using oxytocin. The separation was conducted with a mobile phase system consisting of water/acetonitrile+0.1% TFA. The injection solution was prepared by dissolving 10 mg oxytocin in 1 mL water+0.1% TFA. 500 μL of this sample solution was injected, and the peptide was separated by applying the gradients shown in Table 2. The relative load of this separation was 2 mg/$g_{packing\ material}$.

The elution gradients are given in Table 2 below

TABLE 2

| A) "100%" aqueous loading conditions | | | B) control (water/acetonitrile 90/10) | | |
|---|---|---|---|---|---|
| t/[min] | flow [mL/min] | % by volume acetonitrile | t/[min] | flow [mL/min] | % by volume acetonitrile |
| 0 | 0.5 | 0 | 0 | 0.5 | 10 |
| 15 | 0.5 | 0 | 15 | 0.5 | 10 |
| 15.1 | 0.5 | 10 | 15.1 | 0.5 | 16 |
| 30 | 0.5 | 10 | 95.1 | 0.5 | 24 |
| 30.1 | 0.5 | 16 | 140 | 0.5 | 70 |
| 110.1 | 0.5 | 24 | | | |
| 140 | 0.5 | 70 | | | |

Figure 3A:
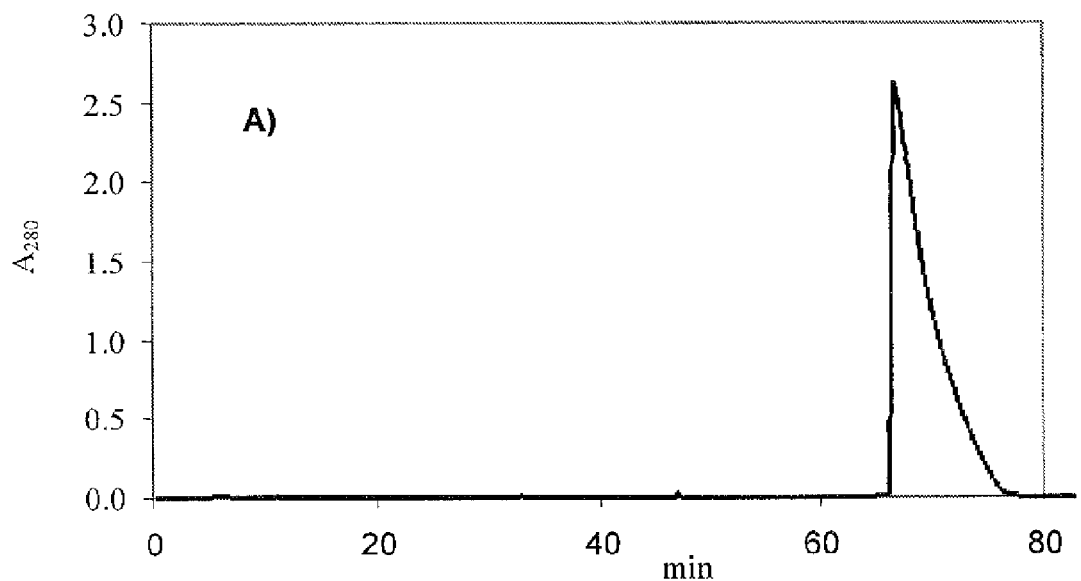
Figure 3B:
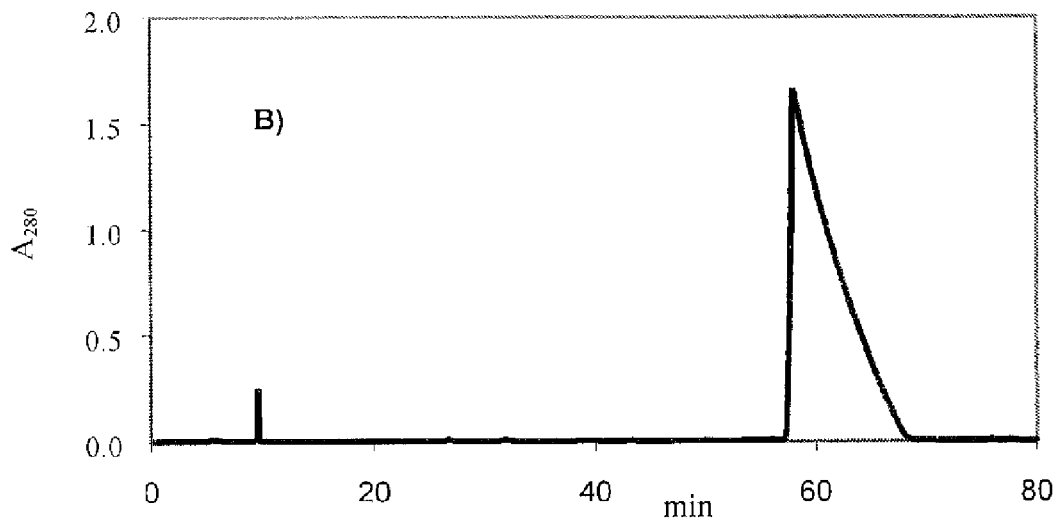

The chromatograms are represented in FIG. 3, on which:
FIG. 3A is the chromatogram obtained in the following loading conditions: loading in water+0.1% TFA
FIG. 3B is the chromatogram obtained in the following loading conditions: loading in water/acetonitrile 90/10 by volume+0.1% TFA Example 3

Repeated Separations

This example shows that "100%" aqueous loading conditions can be used repeatedly without loosing the effect of post-column pressure. Preparative chromatography of insulin was used.

A KR100-16-C18 column (4.6×250 mm, packing density: 0.6 g/mL) was purged 5 min with (aqueous 100 mM NH$_4$Ac)/acetonitrile 30/70 with a post-column overpressure of 2.7 MPa. Then it was equilibrated with 10 column volumes of "100%" aqueous phases with buffer 100 mM NH$_4$Ac at pH 4.0 and at flow 0.5 mL/min, with a post-column overpressure of 2.7 MPa. Then 100 μL of human insulin solution (10 mg human insulin/mL aqueous 200 mM HAc) was injected. Such an injection corresponds to a relative loading of 0.4 mg/$g_{packing\ material}$. The gradient elutions are shown in Table 3.

TABLE 3

| t/[min] | flow [mL/min] | % by volume acetonitrile |
|---|---|---|
| 0 | 0.5 | 0 |
| 4.9 | 0.5 | 0 |
| 5 | 0.5 | 10 |
| 14.9 | 0.5 | 10 |
| 15 | 0.5 | 20 |
| 95 | 0.5 | 32 |
| 95.1 | 0.5 | 70 |

Figure 4:
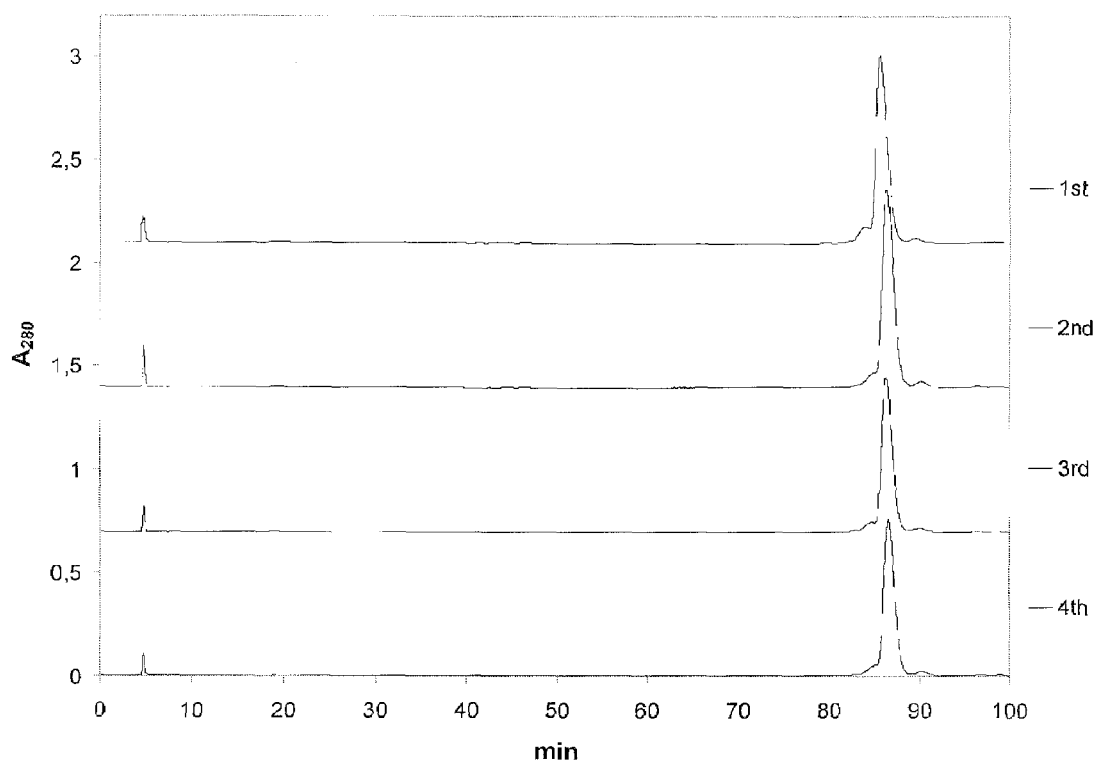

Chromatograms were recorded at 280 nm. The separation was repeated 4 times with same conditions. All four separations gave the same result as can be seen in FIG. 4. Chromatograms also demonstrate that the moderately overloaded preparative injection of insulin was well retained on the C18 column when loaded under "100%" I aqueous conditions.

Example 4

Insulin Separations Using No Post-Column Overpressure

This example shows how preparative separation of insulin deteriorates when no post-column pressure is used at "100%" aqueous loading condition. Other conditions are same as in Example 1.

A KR100-10-C8 column (4.6×250 mm, packing density: 0.6 g/mL) was equilibrated with 10 column volumes of the following aqueous phases:
A: "100%" aqueous phase: water+0.1% TFA;
C: "100%" aqueous phase: 50 mM NH$_4$Ac at pH 4.5;
at 0.5 mL/min, with a negligible post-column overpressure (less than 0.1 MPa).

Then 500 μL of human insulin solution (10 mg human insulin/mL water+0.1% TFA) was injected. Such an injection corresponds to a relative loading of 2 mg/$g_{packing\ material}$. The gradient elution is shown in Table 1, Example 1.

Figure 5A:
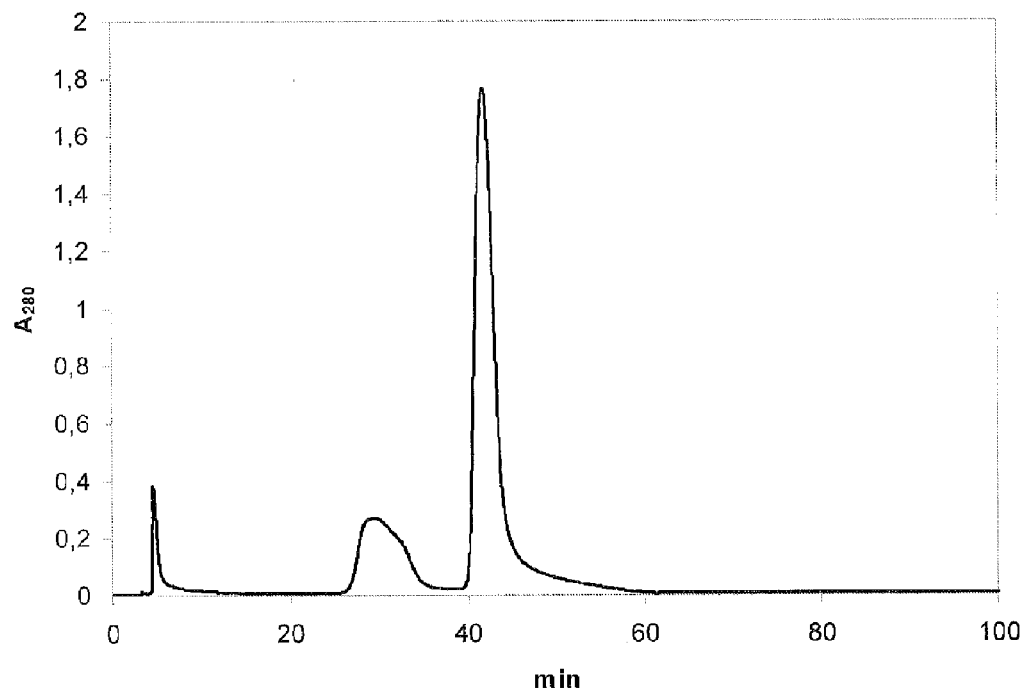
Figure 5B:
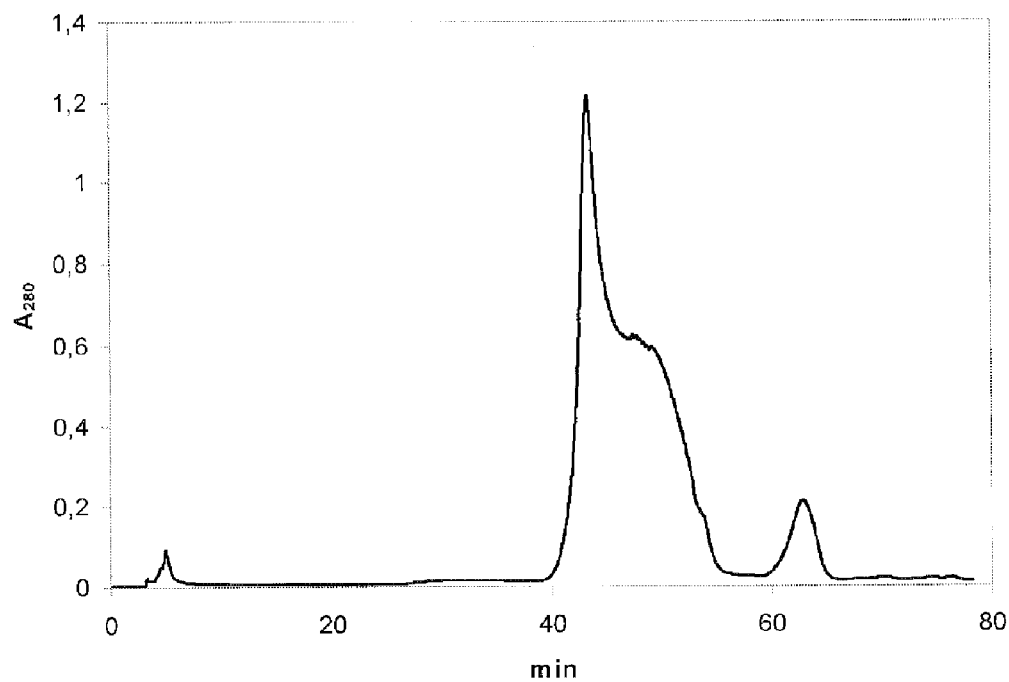

Chromatograms were recorded at 280 nm and are presented in FIG. 5, on which:
FIG. 5A is the chromatogram obtained with mobile phase A as loading solution, and,
FIG. 5B is the chromatogram obtained with mobile phase C as loading solution.

Each chromatogram shows two large peaks which usually would be interpreted as two different compounds. However, in these two chromatograms it was verified by analysing samples collected at retention times of each peak that insulin makes up both peaks. The insulin elutes as strongly distorted and unpredictable peaks. The total width of the parts of chromatograms in FIGS. 5A and 5B where insulin elutes is also much larger than for the cases when a post-column pressure is applied (FIGS. 2A and 2C) where only one insulin peak appears, the peak shape is normal and predictable and the retention time width where insulin elutes is narrow. A narrower peak width gives better ability to separate impurities from product peak, especially when impurities elute close to product peak.

What is claimed is:

1. Method for separating products from a mixture by reversed phase high performance liquid chromatography comprising a loading step and a separation step, using a column packed with a stationary phase which is hydrophobic and a mobile phase (B), wherein the loading step comprises loading said column with an aqueous phase (A) containing said products to be separated while applying an overpressure of at least about 0.3 MPa to all parts of the stationary phase in the column and wherein the overpressure during the separation step is decreased while the amount of organic modifier increases.

2. Method according to claim 1, wherein the aqueous phase (A) is essentially free from organic solvent or organic modifier.

3. Method according to claim 1 wherein the mobile phase (B) consists essentially of water and an organic modifier.

4. Method according to claim 1, wherein an organic modifier is added to the aqueous mobile phase (B) while maintaining the overpressure applied during the loading step.

5. Method according to claim 4, wherein the overpressure is maintained by a pressure-regulating valve in the exit line from said column.

6. Method according to claim 1, wherein before the loading step, the column is flushed with a mobile aqueous phase (C) containing at least 15% by volume of organic modifier, thereafter an overpressure of at least about 0.3 MPa is applied to all parts of the stationary phase in the column and the mobile phase (C) is progressively substituted by an aqueous phase (A) while maintaining said overpressure.

7. Method according to claim 1, wherein the hydrophobic stationary phase is porous silica, which has been modified to partly consist of $R_n SiX_{4-n}$ (n=1, 2 or 3), with each R consisting of an aryl group or an alkyl group. In the case n=2 or 3, each R may consist of the same or different groups, X consisting of —O—Si where Si is a Si-atom, the group $R_n SiX_{4-n}$ (n=1, 2 or 3) is either a part of a porous silica or a part of the added layer resulting from surface modification.

8. Method according to claim 1, wherein the hydrophobic stationary phase is a C8-C18 alkyl-modified stationary phase.

9. Method according to claim 1, wherein the aqueous phase (A) comprises a buffer selected from the group consisting of aqueous solutions of trifluoroacetic acid (TFA), acetic acid, sodium hydroxide, potassium hydroxide, ammonia, tris(hydroxymethyl)aminomethane and mixtures and salts thereof, and aqueous solutions of salts of phosphoric acid, sulfuric acid and hydrochloric acid.

10. The method according to claim 1, wherein the organic modifier is selected from the group consisting of organic solvents miscible with water.

11. Method according to claim 1, wherein the products to be separated are selected from the group consisting of peptides, proteins, polynucleotides, prostaglandins, steroids, vitamins and pharmaceutical active compounds.

12. Method according to claim 1 comprising the successive steps of:
    (a) flushing the column with a mobile phase (C) containing 15-50% by volume of an organic modifier;
    (b) applying an overpressure of at least about 0.3 MPa to all parts of the stationary phase in the column;
    (c) progressively changing the mobile phase (C) to an aqueous phase (A) while maintaining said overpressure;
    (d) loading the water-soluble products to be separated in an aqueous phase (A) while maintaining said overpressure;
    (e) changing mobile phase by adding an organic modifier while maintaining said overpressure;
    (f) starting elution with reduced overpressure or after suppression of the overpressure;
    (g) completing the chromatographic separation.

13. Method according to claim 1, wherein an organic modifier is added progressively to the mobile phase (B).

14. Method according to claim 1, wherein the amount of organic modifier in the mobile phase (B) used in the separation step is from about 3 to about 95% by volume.

15. Method according to claim 1, wherein the organic modifier in selected from the group consisting of alcohols, ketones, esters and ethers.

16. Method according to claim 1, wherein the overpressure is in the range from about 0.3 to about 10 MPa.

17. Method according to claim 16, wherein the overpressure is in the range from about 0.4 to about 5 MPa.

* * * * *

UNITED STATES PATENT AND TRADEMARK OFFICE
CERTIFICATE OF CORRECTION

PATENT NO. : 7,413,658 B2
APPLICATION NO. : 10/904670
DATED : August 19, 2008
INVENTOR(S) : Sylvia Winkel Pettersson et al.

It is certified that error appears in the above-identified patent and that said Letters Patent is hereby corrected as shown below:

| | |
|---|---|
| Claim 7, column 9, line 36 | "$R_n SiX_{4-n}$ (n=1, 2 or 3)," |
| should read | -- $R_n SiX_{4-n}$ (n=1, 2 or 3), -- |
| | |
| Claim 15, column 10, line 36 | "modifier in selected" |
| should read | -- modifier is selected -- |

Signed and Sealed this
Eighth Day of March, 2011

David J. Kappos
*Director of the United States Patent and Trademark Office*